US010117827B2

(12) United States Patent
Lutz et al.

(10) Patent No.: US 10,117,827 B2
(45) Date of Patent: Nov. 6, 2018

(54) PREPARATIONS FOR SUPPRESSING OR ATTENUATING OCULAR IRRITANCY

(71) Applicant: Y&B MOTHER'S CHOICE LTD., Jerusalem (IL)

(72) Inventors: Rachel Lutz, Gush Etzion (IL); Alexander Besonov, Rehovot (IL); Tova Silberstein, Jerusalem (IL)

(73) Assignee: Y&B MOTHER'S CHOICE LTD., Jerusalem (IL)

( * ) Notice: Subject to any disclaimer, the term of this patent is extended or adjusted under 35 U.S.C. 154(b) by 23 days.

(21) Appl. No.: 15/102,402

(22) PCT Filed: Dec. 8, 2014

(86) PCT No.: PCT/IL2014/051068
§ 371 (c)(1),
(2) Date: Jun. 7, 2016

(87) PCT Pub. No.: WO2015/083174
PCT Pub. Date: Jun. 11, 2015

(65) Prior Publication Data
US 2017/0020807 A1 Jan. 26, 2017

(30) Foreign Application Priority Data
Dec. 8, 2013 (IL) .......................... 229836

(51) Int. Cl.
A61K 36/00 (2006.01)
A61K 8/98 (2006.01)
A61K 8/55 (2006.01)
A61Q 5/02 (2006.01)
A61K 8/64 (2006.01)
A61Q 19/00 (2006.01)
A61Q 19/10 (2006.01)
A61K 8/97 (2017.01)
A61K 8/34 (2006.01)
A61K 8/60 (2006.01)
A61K 8/73 (2006.01)
A61K 8/92 (2006.01)

(52) U.S. Cl.
CPC .............. A61K 8/982 (2013.01); A61K 8/345 (2013.01); A61K 8/553 (2013.01); A61K 8/60 (2013.01); A61K 8/64 (2013.01); A61K 8/73 (2013.01); A61K 8/735 (2013.01); A61K 8/92 (2013.01); A61K 8/922 (2013.01); A61K 8/97 (2013.01); A61Q 5/02 (2013.01); A61Q 19/00 (2013.01); A61Q 19/10 (2013.01); A61K 2800/524 (2013.01); A61K 2800/596 (2013.01); A61K 2800/5922 (2013.01); A61K 2800/75 (2013.01)

(58) Field of Classification Search
CPC ...................................................... A61K 36/00
See application file for complete search history.

(56) References Cited

U.S. PATENT DOCUMENTS

| | | | |
|---|---|---|---|
| 2,996,540 | A | 8/1967 | Pearl |
| 4,247,569 | A | 1/1981 | Hata et al. |
| 4,511,555 | A | 4/1985 | Faust |
| 5,080,901 | A | 1/1992 | Hangay et al. |
| 5,397,778 | A | 3/1995 | Forse et al. |
| 5,455,232 | A | 10/1995 | Piljac et al. |
| 5,466,675 | A | 11/1995 | Piljac et al. |
| 5,503,766 | A | 4/1996 | Kulperger |
| 5,514,661 | A | 5/1996 | Piljac et al. |
| 5,639,794 | A | 6/1997 | Emerson et al. |
| 5,817,314 | A | 10/1998 | So et al. |
| 6,475,476 | B1 | 11/2002 | Fluker |
| 6,485,711 | B1 | 11/2002 | Olmstead |
| 6,548,463 | B2 | 4/2003 | Miyahara et al. |
| 7,001,877 | B1 | 2/2006 | Grier |
| 7,129,218 | B2 | 10/2006 | Stipcevic et al. |
| 7,262,171 | B1 | 8/2007 | Piljac et al. |
| 2006/0003022 | A1 | 1/2006 | McNeff et al. |
| 2006/0018867 | A1 | 1/2006 | Kawasaki et al. |
| 2006/0143838 | A1 | 7/2006 | Palpu et al. |
| 2007/0202062 | A1 | 8/2007 | Workman et al. |
| 2007/0231403 | A1 | 10/2007 | Park et al. |
| 2010/0055138 | A1 | 3/2010 | Margulies et al. |
| 2010/0183528 | A1 | 7/2010 | Maloney et al. |
| 2010/0233128 | A1* | 9/2010 | Panasenko ............. A61K 8/922 424/93.4 |
| 2011/0020302 | A1 | 1/2011 | Banov et al. |
| 2011/0052514 | A1 | 3/2011 | Jüsten et al. |
| 2011/0081402 | A1 | 4/2011 | Kojima et al. |
| 2012/0129950 | A1 | 5/2012 | Macinga et al. |

FOREIGN PATENT DOCUMENTS

| | | |
|---|---|---|
| AU | 747088 | 5/2002 |
| CA | 2 460 825 A1 | 9/2005 |
| CA | 2 195 419 C | 1/2008 |

(Continued)

OTHER PUBLICATIONS

U.S. Appl. No. 09/644,984; U.S. Pat. No. 7,262,171.
U.S. Appl. No. 11/701,860.
U.S. Appl. No. 11/881,271; U.S. Pat. No. 7,985,722.
U.S. Appl. No. 11/985,977.
Shiau, et al. "Quantification for Saponin from a Soapberry (*Sapindus mukorossi gaertn*) in Cleaning Products by a Chromatographic and two Colorimetric Assays", J. Fac. Agr., Kyushu Univ., vol. 54, No. 1, pp. 215-221, (2009).
Natural Preservative—Aspen Bark Extract, online at http://www.theherbarie.com/Aspen-Bark-Extract-pr-463.html, four pages, retrieved online Jun. 10, 2013.

(Continued)

Primary Examiner — Qiuwen Mi
(74) Attorney, Agent, or Firm — V

(57) ABSTRACT

Provided is a tear-free formulation for suppressing or reducing ocular irritancy of a pre-made cosmetic or therapeutic formulation or an ophthalmic formulation suitable for application to an eye of a subject or to a skin region surrounding an eye of a subject.

10 Claims, No Drawings

(56) References Cited

FOREIGN PATENT DOCUMENTS

| | | |
|---|---|---|
| CA | 2 129 542 C | 4/2008 |
| CA | 2 378 557 C | 12/2009 |
| CA | 2 321 926 C | 4/2010 |
| CA | 2 658 873 A1 | 9/2010 |
| CN | 1056525 A | 11/1991 |
| CN | 1096918 A | 1/1995 |
| CN | 1240640 A | 1/2000 |
| CN | 1344537 A | 4/2002 |
| CN | 1349792 A | 5/2002 |
| CN | 1370515 A | 9/2002 |
| CN | 101214208 A | 7/2008 |
| CN | 101390816 A | 3/2009 |
| CN | 101554369 A * | 10/2009 |
| CN | 101732208 A | 6/2010 |
| CN | 101978844 A | 2/2011 |
| CN | 102028640 A | 4/2011 |
| CN | 102247309 A | 11/2011 |
| CN | 102319197 A * | 1/2012 |
| CN | 102379836 A | 3/2012 |
| CN | 103598225 B | 7/2015 |
| EP | 1 053 782 A1 | 11/2000 |
| EP | 1 287 742 A1 | 3/2003 |
| EP | 1 889 623 A2 | 2/2008 |
| ES | 2 259 933 A1 | 10/2006 |
| ES | 2 333 574 A1 | 2/2010 |
| FR | 2 730 634 A1 | 8/1996 |
| FR | 2 810 550 A1 | 12/2001 |
| FR | 2 924 123 A1 | 5/2009 |
| JP | 52-125510 A | 10/1977 |
| JP | 60-38317 A | 2/1985 |
| JP | 61-194015 A | 8/1986 |
| JP | 64-68307 A | 3/1989 |
| JP | 6-57298 A | 3/1994 |
| JP | 9-503196 A | 3/1997 |
| JP | 9-249577 A | 9/1997 |
| JP | 10-502925 A | 3/1998 |
| JP | 10-298595 A | 11/1998 |
| JP | 2000-191513 A | 7/2000 |
| JP | 2001322943 A | 11/2001 |
| JP | 2002000447 A | 1/2002 |
| JP | 2002-265327 A | 9/2002 |
| JP | 2002-363065 A | 12/2002 |
| JP | 2003096489 A | 4/2003 |
| JP | 2003-267834 A | 9/2003 |
| JP | 2004-631 A | 1/2004 |
| JP | 2004-331961 A | 11/2004 |
| JP | 2005-289912 A | 10/2005 |
| JP | 2005343883 A | 12/2005 |
| JP | 3860206 B2 | 12/2006 |
| JP | 2007-223905 A | 9/2007 |
| JP | 2008-120745 A | 5/2008 |
| JP | 2009007266 A | 1/2009 |
| JP | 2012-077037 A | 4/2012 |
| KR | 10-2007-0103899 A | 10/2007 |
| KR | 10-0821842 B1 | 4/2008 |
| KR | 10-0821846 B1 | 4/2008 |
| KR | 2010-0077554 A | 7/2010 |
| RO | 110679 B1 | 3/1996 |
| RU | 2 124 899 C1 | 1/1999 |
| RU | 2 126 687 C1 | 2/1999 |
| RU | 2 154 480 C1 | 8/2000 |
| RU | 2 162 701 C1 | 2/2001 |
| RU | 2 179 978 C1 | 2/2002 |
| RU | 2 210 379 C1 | 8/2003 |
| RU | 2 234 913 C1 | 8/2004 |
| RU | 2 247 571 C2 | 3/2005 |
| RU | 2328301 C2 | 7/2008 |
| TW | 200944244 A | 11/2009 |
| WO | 93/14767 A2 | 8/1993 |
| WO | 96/41528 A1 | 12/1996 |
| WO | 98/48768 A1 | 11/1998 |
| WO | 99/43334 A1 | 9/1999 |
| WO | 00/72861 A1 | 12/2000 |
| WO | 01/10447 A1 | 2/2001 |
| WO | 02/092823 A1 | 11/2002 |
| WO | 03/097003 A1 | 11/2003 |
| WO | 2005/099729 A2 | 10/2005 |
| WO | 2006/007741 A1 | 1/2006 |
| WO | 2008/013899 A2 | 1/2008 |
| WO | 2009/153800 A1 | 12/2009 |
| WO | 2012/077119 A2 | 6/2012 |
| WO | 2012/077120 A2 | 6/2012 |

OTHER PUBLICATIONS

Natural Soap Recipe, online at http://www.essortment.com/natural-soap-recipe-38714.html, three pages, retrieved online Jun. 10, 2013.
Osbourn, et al., "The saponins—polar isoprenoids with important and diverse biological activities", Nat. Prod. Rep., vol. 28, pp. 1261-1268, (2011).
Saha, et al., "Structure-biological activity relationships in triterpenic saponins: the relative activity of protobassic acid and its derivatives against plant pathogenic fungi", Pest Manag Sci, vol. 66, pp. 825-831, (2010).
Huang, et al., "Triterpenoid saponins from the fruits and galls of Sapindus mukorossi", Phytochemistry, vol. 69, pp. 1609-1616, (2008).
Sea Kelp Moisturizer (high performance anti-aging moisturizer); online at http://www.benaturalorganics.com/details-sea-kelp-moisturizer.html, two pages, retrieved online Jun. 10, 2013.
Murgu, et al., "Dereplication of Glycosides from Sapindus saponaria using Liquid Chromatography-Mass Spectrometry", J. Braz. Chem. Soc., vol. 17, No. 7, pp. 1281-1290, (2006).
International Search Report for International Application No. PCT/IL2011/050053, three pages, dated Nov. 27, 2012.
International Search Report for International Application No. PCT/IL2011/050054, four pages, dated Mar. 1, 2013.
Chen et al., "Chemical constituents in Populus davidiana", Chinese Traditional and Herbal Drugs, vol. 37, No. 6, pp. 816-818, (2006). English Abstract on p. 816.
Lin, "The flavour component and antimicrobiol insecticidal functiond of Wasabi", China Condiment, vol. 1, No. 1, pp. 12-14 and 23, (2004). English Abstract on p. 12.
Tang et al., "Bioactivities and Application Research of Saponin from Pericarps of Sapindus mukorossi", Nat Prod Res Dev, vol. 19, pp. 562-565, (2007). English Abstract on p. 562.
Zhao et al., "Study on honeysuckle antimicrobial extraction and antimicrobial effect", Journal of Shaoyang College, vol. 14, No. 3, pp. 204-209, (2001). English Abstract on p. 209.
U.S. Appl. No. 13/992,309.
U.S. Appl. No. 115/262,400.
Bryan, "How to use egg for hair growth", Aug. 16, 2013, XP002736508.
Peyman, "Serum lactescence in normal subjects and in patients with coronary artery disease before and after the administration of sublingual heparin", Am. Heart J., vol. 62, No. 5, pp. 676-679, (1961).
Shelton, "DIY Egg Shampoo", Dec. 30, 2012, XP002736571.
Abeytunga et al., "Structure-Antibacterial Activity Relationship of Some Aromatic Acids", J. Natn. Sci. Coun. Sri Lanka, vol. 26, No. 2, pp. 133-139, (1998).
Guzman, "Natural Cinnamic Acids, Synthetic Derivatives and Hybrids with Antimicrobial Activity", Molecules, vol. 19, pp. 19292-19349, (2014).
Li et al., "Analysis and evaluation of essential oil components of cinnamon barks using GC-MS and FTIR spectroscopy", Industrial Crops and Products, vol. 41, pp. 269-278, (2013).
Paranagama et al., "A Comparison of Essential Oil Constituents of Bark, Leaf, Root and Fruit of Cinnamon (*Cinnamomum zeylanicum blum*) Grown in Sri Lanka", J. Natn. Sci. Foundation Sri Lanka, vol. 29, Nos. 3 & 4, pp. 147-153, (2001).
Pastarova et al., "Analytical Study of Free and Ester Bound Benzoic and Cinnamic Acids of Gum Benzoin Resins by GC-MS and HPLC-frit FAB-MS", Phytochemical Analysis, vol. 8, pp. 63-73, (1997).

(56) References Cited

OTHER PUBLICATIONS

Pundir et al., "Evaluation of five chemical food preservatives for their antibacterial activity against bacterial isolates from bakery products and mango pickles", J. Chem. Pharm. Res., vol. 3, No. 1, pp. 24-31, (2011).
Shin et al., "Bactericidal activity of wasabi (*Wasabia japonica*) against Helicobacter pylori", 94 (2004) 255-261.
Aneja et al., "In Vitro Antimicrobial Actitvity of Sapindus mukorossi and Emblica officinalis Against Dental Caries Pathogens", Ethnobotanical Leaflets, 14: 402-412, 2010. Jan. 4, 2010.
Silici et al., "Chemical compostion and antibacterial activity of propolis collected by three different races of honeybees in the same region", 99 (2005) 69-73.

* cited by examiner

PREPARATIONS FOR SUPPRESSING OR ATTENUATING OCULAR IRRITANCY

TECHNOLOGICAL FIELD

The invention generally relates to natural preparations for suppressing or attenuating ocular irritancy.

BACKGROUND

Formulations such as cleansing formulations (e.g. shampoos, facial soaps, etc.) generally cause irritation to the ocular membrane when coming in contact with the eyes. This imposes an unpleasant feeling to the user, which results in stinging or tearing, and in certain cases may even be harmful. This problem is of particular importance in shampoos designated for use by infants and children.

Cleansing formulations are irritating mainly because they comprise surfactants, especially ionic surfactants, which interact with the mucous membrane, and because the pH of such formulation differs from the normal pH of the eye being 7.0 to 7.3.

Recent studies conducted by the U.S. environmental protection agency (EPA) revealed that human blood and lipid tissues contain up to 400 hazardous chemicals originating from cosmetics and food products. Those chemicals may cause various side effects, such as headaches, eye irritation, skin irritation, and long term effects such as the development of various cancer diseases.

Such studies have encouraged the development of "natural" cosmetic compositions; however, to date, none of the available compositions are 100% natural body soaps/shampoos. Several of the products known today contain mainly synthetic ingredients, with the addition of a very small amount of natural ingredients. Other known products contain a higher percentage of natural ingredients; however, they are mainly composed of synthetic materials. The most natural known products today contain chemically modified natural ingredients.

Products composed of natural ingredients may also contain irritating substances that cause tear, itching and redness in the eye when coming in contact with the ocular membrane. Thus, problems associated with the development of a product that is wholly natural become vastly more complex where the product must also demonstrate no irritancy to the user's eyes. This development is particularly important in products intended for use in babies and young children.

WO2012/077120 discloses natural formulations for skin or hair for providing cleansing, moisturizing, minimizing skin imperfections, reducing skin oiliness, providing fragrance to the hair or skin and reliving skin dryness and signs of aging.

FR2810550 discloses solutions for use in medicine containing homogeneous extracts of the white and yolk of quail eggs for the treatment of allergies such as eye irritation.

ES2333574 discloses natural compositions for treating skin irritation containing chicken egg yolk.

General Description

The inventors of the present invention have developed a class of products comprising a combination or a mixture of naturally occurring ingredients which has a suppressing or attenuating effect on the ocular irritancy of formulations which come into contact with ocular membranes; such formulations were found to be useful on cosmetic formulations as well as on therapeutic formulations such as, for example, shampoos, conditioners, soaps, make-up removers, eye-drops, and others.

The preparations of the invention have been found to be efficient in suppressing or attenuating ocular or skin irritancy, per se, and also endow other formulations which are known or expected to have a degree of irritancy with reduced or diminished irritating effects.

Thus, in accordance with a first aspect of the invention, there is provided a formulation comprising a combination of lecithin and egg yolk, at least one natural oil, and optionally hyaluronic acid and/or hyaluronate, said formulation being capable of reducing, diminishing or ameliorating irritation to an eye region or to a skin region surrounding the eye.

In another aspect, the invention provides a formulation comprising a combination of lecithin and egg yolk, at least one natural oil, and optionally hyaluronic acid and/or hyaluronate, said formulation being capable of reducing, diminishing or ameliorating irritation to an eye.

In a further aspect, the invention provides a formulation comprising
1—at least one of lecithin and egg yolk,
2—at least one natural oil, and
3—optionally hyaluronic acid and/or hyaluronate,
said formulation being adapted for adding to a skin care formulation or hair care formulation exhibiting irritation to an eye region or to a skin region surrounding the eye, the formulation capable of reducing, diminishing or ameliorating irritation caused by the skin care formulation coming in contact with the eye region or the skin region surrounding the eye.

The low irritancy formulation is thus herein classified as a minimally or non-irritating formulation. As known in the field of the invention, such formulations are typically known as "tear-free" formulations.

The low irritancy formulation may thus be used as a baby shampoo, baby bath, mild skin cleanser, facial skin cleanser, sensitive skin cleanser and other cleansing formulations suitable for use on infant skin.

The formulations of the invention may similarly be utilized on human infant and adult skin regions, eyes, or skin regions surrounding the eyes.

In another aspect, the formulation comprising at least one of lecithin and egg yolk, at least one natural oil, and optionally hyaluronic acid and/or hyaluronate may be used for any purpose in which low irritancy to the skin and/or eyes is desirable. The formulation may for example be utilized as an additive (add on) to formulations which are irritating to the (human or non-human) eyes or skin; thereby rendering such irritating formulations with a reduced or diminished irritancy.

In some embodiments, the formulation is selected from a baby shampoo, baby bath, mild skin cleanser, facial skin cleanser, sensitive skin cleanser and cleansing formulations suitable for use on human infant skin; or adult shampoo, adult bath, mild skin cleanser, facial skin cleanser, sensitive skin cleanser and cleansing formulations suitable for use on human adult skin.

In a further aspect, the invention pertains to the use of any one of the above minimally or non-irritating formulations for the preparation of an additive to an existing formulation, for reducing, diminishing or ameliorating irritation to an eye or a skin region surrounding the eye.

According to the invention, the formulation comprising the naturally occurring ingredients recited hereinabove or below, is adapted to produce the herein referred to non-irritating additive or additive. According to some embodiments, the additive may be stored before it is added to an eye-irritating formulation.

As may be clear to the skilled in the art, the additive of the invention does not substantially alter any one existing characteristics of an irritating formulation, apart from rendering it less irritating or not irritating at all. In other words, properties such as cleaning properties, foaming e.g., of a shampoo formulation, ease of removal by washing, feeling and after-feeling effects are not significantly reduced or attenuated by the addition of a formulation of the invention.

The invention also pertains to a method for suppressing or reducing ocular irritancy of a cosmetic or therapeutic formulation suitable for application to an eye of a subject or to a skin region surrounding an eye of a subject, the formulation being capable of causing irritation to an ocular membrane, the method comprising: mixing prior to application of said formulation to the eye or a skin region surrounding said eye an effective amount of an additive, as defined herein.

The formulations and additives of the invention are capable of suppressing, reducing, delaying, or diminishing any one or more irritating feeling in the eyes of a subject; said irritating feeling being associated with one or more component or ingredient present in a cosmetic or therapeutic formulation to be applied to the eye or a skin region surrounding the eye.

The additive may be applied to the eye prior to, concomitant with or after a cosmetic or therapeutic formulation has been applied to the eye or a skin region surrounding the eye. The additive is typically applied to the cornea of the eye. In some embodiments, the additive is added and mixed into the cosmetic or therapeutic formulation during the manufacture process of said cosmetic or therapeutic formulation; thus rendering said cosmetic or therapeutic formulation tear-free.

Thus, the additive may be in the form of an add-on formulation which may be added to a ready-made cosmetic or therapeutic formulation or may be the cosmetic or therapeutic formulation itself.

It is thus a further object of the invention to provide a non-skin-irritating or non-eye-irritating formulation, either formulation being selected from a cosmetic formulation for application onto a skin region of a subject, a cleansing formulation, a therapeutic topical formulation, an ophthalmic formulation, a solid form formulation or a liquid form formulation, and a cleansing, or therapeutic formulations suitable for infants and children.

As stated above, the formulations of the invention are all natural formulations, namely comprising components and ingredients originating or extracted or obtained or derived from nature. No synthetic ingredients are included in formulations of the invention.

The "lecithin" comprised in formulations of the invention is typically derived from animal or plant sources such as soy beans, eggs, milk, marine sources, rapeseed, cottonseed, and sunflower. In some embodiments, the lecithin is derivable from soy beans and/or egg yolk.

The "natural oils" are typically selected from almond oil, aragan oil, avocado oil, calendula oil, castor oil, coconut oil, grape seed oil, jojoba oil, linseed oil, macadamia oil, meadowfoam oil, olive oil, palm oil, sesame seed oil, sun flower oil, vegetable squalane and squalane, oil from eggs or yolk, jojoba wax and lanolin.

In some embodiments, the natural oils are selected from castor oil, jojoba oil, jojoba wax, meadowfoam oil, vegetable squalane and squalane, oil from eggs or yolk, lanolin, bees wax, carnauba wax, candelilla wax, cocoa and animals wax/butter.

In some embodiments, the formulations according to the invention comprise at least one additional additive selected amongst phospholipids (lecithins), polysaccharides, polyols, saponins, salicilates, preservatives, perfumes, natural coloring agents, emollients, non-aqueous or aqueous solvents or mixtures, and other active or non-active components.

In some embodiments, a formulation according to the invention comprises one or more phospholipids and/or one or more polysaccharide.

In some embodiments, the formulation further comprises at least one emollient and/or at least one polyol. The polyol is selected from mannitol, glycerol, zemea, trehalose, fructose, mannose, sucrose, glucose, dextrose, trehalose, mannitol, lactose, rhamnose, sorbitol, honey extracts, glycol, diols and polyols such as vegetable glycerin, 1,2-butanediol, propylene glycol, ethanol. Other polyols included are betaine, natural urea, lactic acid and other alpha hydroxy acids.

In some embodiments, the polyol is selected from mannitol, glycerol, zemea and trehalose.

In some embodiments, the phospholipid is soy bean lecithin.

In some embodiments, the polysaccharide is selected, in a non-limiting fashion, from xanthan, Tragacanth gum, Carrageenan gum, Alginates, Konjac gum Agar-Agar, gum Arabic, Guar gum, Starch, Gellan gum, Pectin, Cellulose, Welan and Dituan gum, Locust bean gum, Dammar gum, Kauri gum, Spruce gum, Fenugreek gum and gum anima, *sclerotium* gum and poly glutamic acid.

In some embodiments, the polysaccharide is selected from sodium hyaluronate, xanthan gum, Carrageenan, Konjac gum, Tragacanth gum, Alginates, Guar gum, Locust bean gum, *sclerotium* gum, and poly glutamic acid In some embodiments, the emollient is a natural oil selected from jojoba oil and squalene oil.

In some embodiments, the formulation comprises at least one phospholipid, at least one polysaccharide and at least one emollient.

In some embodiments, the formulation according to the invention is the formulation shown in Table 1:

TABLE 1

| A formulation according to the invention | |
|---|---|
| Ingredient | Chemical Family |
| Soy-bean Lecithin | Phospholipids |
| Jojoba oil | Emollient |
| Squalene oil | Emollient |
| Egg Yolk | Phospholipids + cholesterol + Emollient |
| Sodium Hyaluronate | Polysaccharides |

In some embodiments, the sodium hyaluronate may be replaced or combined with at least one other polysaccharide, as exemplified in Table 2.

TABLE 2

| A formulation according to the invention | |
|---|---|
| Ingredient | Chemical Family |
| Soy-bean Lecithin | Phospholipids |
| Jojoba oil | Emollient |
| Squalene oil | Emollient |
| Egg Yolk | Phospholipids + cholesterol + Emollient |

TABLE 2-continued

A formulation according to the invention

| Ingredient | Chemical Family |
|---|---|
| Sodium Hyaluronate and/or Xanthan gum and/or Carrageenan | Polysaccharides |

In some embodiments, the formulation may comprise one or more polyol. In some embodiments, the formulation comprises at least one phospholipid, at least one polysaccharide, at least one polyol and optionally at least one emollient.

In some embodiments, the formulation may comprise at least one preservative.

In other embodiments, the formulation may comprise at least one saponin. In such embodiments, the formulation may comprise at least one phospholipid, at least one polysaccharide, at least one saponin and optionally at least one emollient and/or at least one polyol.

Exemplary formulations are depicted in Table 3 and Table 4.

TABLE 3

A formulation according to the invention

| Ingredient | Chemical Family |
|---|---|
| Soy-bean Lecithin | Phospholipids |
| Jojoba oil | Emollient |
| Squalene oil | Emollient |
| Egg Yolk | Phospholipids + cholesterol + Emollient |
| Mannitol and/or Glycerol and/or Zemea and/or Trehalose | Poly-ol |

TABLE 4

A formulation according to the invention

| Ingredient | Chemical Family |
|---|---|
| Soy-bean Lecithin | Phospholipids |
| Jojoba oil | Emollient |
| Squalene oil | Emollient |
| Egg Yolk | Phospholipids + cholesterol + Emollient |
| Sodium Hyaluronate and/or Xanthan gum and/or Carrageenan | Polysaccharides |
| Mannitol and/or Glycerol and/or Zemea and/or Trehalose | Poly-ol |

In some embodiments, each of the formulations of the invention, e.g., those depicted in Tables 1-4 comprises at least one saponin.

As used herein, the at least one "saponin" is at least one naturally obtained saponin compound or saponin material, as known in the art. When isolated from a natural source, the at least one saponin may be used in its substantially pure form (namely at least 85%, 87%, 92%, 95%, or 98% purity), or may be used as a saponin-containing extract isolated by a method known in the art or by a method of the invention, as disclosed herein.

In some embodiments, the saponin material is a purified compound of the saponin family.

In other embodiments, the saponin material is a saponin-containing extract. In accordance with the present invention, the saponin-containing extract (herein referred to for the purpose of brevity as "saponin extract") contains at least between 0.2% and 95 wt % saponins, out of the total weight of the dry content of the extract. In some embodiments, the extract used in accordance with the present invention comprises between 0.2% and 99 wt % saponins out of the total weight of the dry content of the extract.

In some embodiments, the extract used in accordance with the present invention comprises between 10% and 80 wt % saponins out of the total weight of the dry content of the extract. In other embodiments, the extract used in accordance with the present invention comprises between 10% and 60 wt % saponins out of the total weight of the dry content of the extract. In further embodiments, the extract used in accordance with the present invention comprises between 10% and 50 wt % saponins out of the total weight of the dry content of the extract. In additional embodiments, the extract used in accordance with the present invention comprises between 10% and 40 wt % saponins out of the total weight of the dry content of the extract. In still additional embodiments, the extract used in accordance with the present invention comprises between 10% and 30 wt % saponins out of the total weight of the dry content of the extract.

In some embodiments, the extract used in accordance with the present invention comprises between 10% and 20 wt % saponins out of the total weight of the dry content of the extract.

In some embodiments, the extract used in accordance with the present invention comprises between 0.2% and 10 wt % saponins out of the total weight of the dry content of the extract.

The saponin-containing extract may be obtained from any natural source known to comprise saponins. Such natural source may be a plant source, some of which are detailed infra, and also from non-plant sources such as animal sources and marine organisms, such as starfish and sea cucumbers. In some embodiments of the invention, the saponins are extracted from a plant source, naturally grown or genetically modified to have high saponin content.

In some embodiments of the invention, the saponin material is obtained by extraction from a plant source by employing water, alcohol or a water/alcohol solution. In some embodiments, the alcohol is ethanol or methanol.

In some embodiments, the extraction is achieved by employing a water/alcohol solution. In some embodiments, the water/alcohol solution has a water:alcohol ratio of between 80:20 to 20:80. In further embodiments, the water/alcohol solution has a water:alcohol ratio of between 60:40 to 40:60. In further embodiments, the water/alcohol solution has a water:alcohol ratio of between 70:30 to 30:70. In further embodiments, the water/alcohol solution is 80:20 water/alcohol, 60:40 water/alcohol, 50:50 water/alcohol, 40:60 water/alcohol ratio, 20:80 water/alcohol, 70:30 water/ethanol or 30:70 water ethanol.

The extraction time may vary without limitation from 2 to 8 hours, at or above room temperature (20° C.-30° C.), e.g., above 30° C., 40° C., 50° C. or 60° C. In some embodiments, the extraction is carried out at a temperature between 30° C. and 70° C.

In some embodiments, the saponin material is obtained from a plant source. The plant source may be selected from shikakai, soy beans, beans, peas (*Pisum sativum*), lucerne, tea, spinach, sugar beet, *quinoa*, liquorice, sunflower, horse chestnut, ginseng, oats, *capsicum* peppers, aubergine, tomato seed, alliums, asparagus, yam, fenugreek, *yucca* and ginseng, lucerne, mung beans, *Bupleurum falcatum*, *Camellia oleifera*, *Camellia sinensis Desmodium adscendens*, *Gypsophila*, *Panax quinqufolius*, *Panax japonicas*, *Quillaja saponaria*, *Sapindus delavayi*, *Sapindus mukorossi*, *Sapindus marginatus*, *Sapindus saponaria*, *Sapindus trifoliatus*, *Saponaria officinalis*, *Styrax japonica*, and *Yucca schidigera* or any mixture thereof. Any part of the plant may be used for extracting the saponin material, including leaves, stems, roots, bulbs, blossom and fruit (including the skin, flesh and seed of the fruit).

In some embodiments, the saponin material is an extract of *Camellia oleifera*, *Saponaria officinalis*, or *Sapindus mukorossi* or a mixture thereof.

In other embodiments, the saponin material is an extract of *Camellia oleifera*, or *Sapindus mukorossi* or a mixture thereof.

In other embodiments, the saponin material is an extract of *Sapindus mukorossi*.

The saponin material obtained from a plant source, e.g., *Camellia oleifera*, and/or *Sapindus mukorossi*, may be extracted by treating the plant source in a water/alcohol solution under conditions permitting extraction of the saponin material into the solution. The so-extracted saponin containing material may optionally thereafter be purified by any means known in the art, including: filtration, centrifugation, re-crystallization, distillation, adsorption, chromatographic methods, fractionation, etc.

In some embodiments, the plant source is first dried and ground before being treated in the water/alcohol solution.

In some embodiments, the saponin material is extracted from a plant source following a method comprising:
1. Treating the plant source in a 40:60 to 60:40 water:alcohol solution for a period of time and under conditions permitting extraction of the saponin material from said plant source into said solution, as defined hereinabove;
2. optionally, drying said saponin-containing solution to obtain a saponin-containing solid material; and
3. optionally, purifying said saponin-containing solid material.

In some embodiments, the water:alcohol solution employed is about 50:50.

In some embodiments, the plant source is one or both of *Camellia oleifera* and *Sapindus mukorossi*. In some embodiments, the plant source is *Sapindus mukorossi* and the saponin material is extracted from the nut shell. In other embodiments, the plant source is *Camellia oleifera* and in some embodiments the saponin material is extracted from the defatted seed meal of *Camellia oleifera*.

In some embodiments, the formulation of the invention is a cosmetic formulation comprising an additive according to the invention.

In other embodiments, the formulation of the invention is a therapeutic formulation comprising an additive according to the invention.

In some embodiments, the additive is selected from the formulations listed in Table 1, Table 2, Table 3 or Table 4 above.

In some embodiments, and for the purpose of demonstrating a cosmetic formulation according to the invention, in Table 5, a shampoo formulation is provided:

TABLE 5

A shampoo formulation according to the invention.

| Ingredient | Chemical Family |
|---|---|
| *Sapindus Mukorossi* extract and/or *Camellia oleifera* extract and/or *Quillaja* extract | Saponins |
| Aspen bark (*Populus tremuloides*) extract | Salicaceae |
| Soy-bean Lecithin | Phospholipids |
| Jojoba oil and/or Squalene oil | Emollient |
| Egg Yolk | Phospholipids + cholesterol + Emollient |
| Sodium Hyaluronate and/or Xanthan gum and/or Carrageenan | Poly saccharides |
| Mannitol and/or Trehalose and/or Zemea and/or Glycerol | Poly-ol |

In some embodiments, an exemplary shampoo of the invention is provided in Table 6:

TABLE 6

A shampoo formulation according to the invention

| Ingredient | Chemical Family | Conc. Range wt % |
|---|---|---|
| *Sapindus Mukorossi* extract | Saponins | 0.5-6 |
| *Camellia oleifera* extract | Saponins | 0-6 |
| *Quillaja* extract | Saponins | 0-6 |
| Aspen bark (*Populus tremuloides*) extract | Salicaceae | 0.1-0.8 |
| Soy-bean Lecithin | Phospholipids | 0.1-5 |
| Jojoba oil | Emollient | 0.2-4 |
| Squalene oil | Emollient | 0.2-4 |
| Egg Yolk | Phospholipids + cholesterol + Emollient | 0.2-5 |
| Sodium Hyaluronate | Poly saccharides | 0-0.8 |
| Xanthan gum | Poly saccharides | 0-2.5 |
| Carrageenan | Poly saccharides | 0-2.5 |
| Mannitol | Poly-ol | 0-2.5 |
| Glycerol | Poly-ol | 0-15 |
| Zemea | Poly-ol | 0-15 optional |
| Trehalose | Poly-ol | 0-2.5 optional |
| Perfume | | 0-1.5 |

A shampoo formulation of Table 6 is hereinbelow referred to as Shampoo no. 1 (see experimental details below).

In some embodiments, the formulations of the invention comprise a selection of natural ingredients selected from at least one saponin material; at least one phospholipid; at least one emollient; at least one poly saccharide; and at least one alcohol or polyol. Depending on the nature of the formulation, it may further comprise at least one therapeutic agent; at least one coloring agent; at least one solvent, excipient or diluents.

The formulation may be in the form of a solid or liquid ready for use formulation.

Any additive formulation according to the invention may be used as a formulation for reducing irritation of a ready-made formulation for application onto a skin or membrane tissue region of a subject. Thus, the formulations of the invention are also applicable to reduce or diminish irritations of a skin region by a formulation suitable for application on such a region. The formulations of the invention are not solely applicable for reduction of irritation in the eye.

DETAILED DESCRIPTION OF EMBODIMENTS

Methods

Evaluation of the Suppression or Attenuation of Ocular Irritancy

The suppression of the ocular irritancy of a formulation which comes in contact with an ocular membrane by the addition of the additive of the invention to the formulation can be tested using one of several commonly used methods, including the Draize eye test, Bovine Cornea Opacity Test (BCOP), Isolated chicken eye test (ICE), hens egg chorioallantoic membrane (HET-CAM) assay, epithelial model cultivated from human corneal cells. A combination of several tests other than the Draize eye test is considered to provide reliable replacement for the animal Draize eye test.

Bovine Cornea Opacity Test (BCOP)

The BCOP test can be performed by following the procedure in the OECD Guidelines for the Testing of Chemicals, Section 4 test no. 437 or Pierre Gautheron et al. *Fundamental and Applied Toxicology* 1992 18, 442-449. The BCOP test uses isolated corneas from the eyes obtained as a by-product from abattoirs. Each treatment group (test substance, negative/positive controls) consists of a minimum of three eyes where the cornea has been excised and mounted to a holder. The critical factor while applying the formulations which comprise the no-tear additive (or the control formulations) is ensuring that the test solution adequately covers the epithelial surface. Irritancy effects to the cornea are measured as permeability to fluorescein and opacity, which when combined gives an In Vitro Irritancy Score (IVIS) for each treatment group. Permeability is determined by measuring the amount of fluorescein dye that penetrates through the cornea. Opacity is determined by measuring the amount of light transmitted through the cornea. A substance that induces an IVIS equal to or higher than 55.1 is defined as a corrosive or severe irritant.

Isolated Chicken Eye Test (ICE)

The ICE test can be performed by following the procedure in the OECD Guidelines for the Testing of Chemicals, Section 4 test No. 438. Similarly to the BCOP test, The ICE method uses eyes collected from chickens obtained from slaughterhouses where they are killed for human consumption. The eye is enucleated and mounted in an eye holder with the cornea positioned horizontally. The test substance and negative/positive controls are applied to the cornea. Toxic effects to the cornea are measured by a qualitative assessment of opacity, a qualitative assessment of damage to epithelium based on fluorescein retention, a quantitative measurement of increased thickness (swelling), and a qualitative evaluation of macroscopic morphological damage to the surface. The endpoints are evaluated separately to generate an ICE class for each endpoint, which are then combined to generate an Irritancy Classification for each test substance.

Hens Egg Chorioallantoic Membrane (HET-CAM) Assay

Hen eggs are placed in commercial incubators. On day 10 of development, the eggs are removed from the incubator and candled to determine the viability of the embryo. A rectangular window is removed from the shell directly over the air cell and the egg membrane is carefully moistened with 2-3 ml 0.9% saline and returned to the incubator.

The eggs are then dosed and observed continuously for 5 minutes for the appearance of lysis, hemorrhaging and/or coagulation which is documented.

In addition, the eggs are scored for severity at 1 and 5 minutes. The severity of each reaction after 1 and 5 minutes is recorded.

Human Corneal Epithelial Cell Line

An immortalized human corneal epithelial (HCE) cell line was purchased from ATCC Company. HCE cells were established by infecting primary human corneal epithelial cells with a recombinant SV40-adenovirus vector and by cloning three times to obtain a continuously growing cell line. Initially, HCE cells were grown in a culture medium containing 1 vol of Dulbecco's modified Eagle's medium and 1 vol of Ham's nutrient mixture F-12 supplemented with 15% (vol/vol) fetal bovine serum, 1% (vol/vol) antibiotic, antimycotic solution (penicillin 10,000 U/ml, streptomycin 10,000 mg/ml and amphotericin B 25 mg/ml), 2 mM L-glutamine, 5 mg/ml insulin, 10 ng/ml human epithelial growth factor, 0.5% (vol/vol) dimethylsulfoxide (DMSO, Sigma). For cytotoxicity testing, HCE cells were grown in the same medium and plated at a density of 15,000-30,000 cells/well in a 96-well microtiter plate. The cells were exposed to the test compound-containing medium 24 hours after plating (before the cell culture started to form multilayers and became confluent).

Human cells were incubated in an appropriate medium with the diluted shampoo samples (1:75) for 10 min, and were compared with negative (SLES) and positive controls (saline). After 24 hour incubation at 37° C. under 75% humidity and 5% $CO_2$ atmosphere, the cells were examined for viability by the MTT method (see Mosmann, T. Rapid colorimetric assay for cellular growth and survival: Application to proliferation and cytotoxicity assays. *J. Immunol Methods.*, 1983 65: 55-63). To this end (3-(4,5-dimethylthiazol-2-yl)-2,5-diphenyltetrazolium bromide from Sigma Israel was added to the medium. The calorimetric measurement was performed by an ELISA reader.

Example 1

*Sapindus Mukorossi* Extract Concentration

HCE cell line was exposed to three shampoo formulations: the shampoo formulation of Table 6 (herein referred to as Shampoo No. 1) having an amount *Sapindus mukorossi* extract of 2.25 weight %, and two other Shampoo formulations, Shampoo No. 2 and Shampoo No. 3 which deviate from Shampoo No. 1 in the concentration of *Sapindus mukorossi* extract by having 1.5 and 3.0 wt %, respectively. The HCE cell line was exposed to of Shampoo No. 1 at room temperature such that 50% of the ECH cell line remained viable. The HCE cell line was then exposed to each one of Shampoo No. 2 and Shampoo No. 3, respectively at the same conditions which it was exposed to Shampoo No. 1 and the viability percentage of the HCE cell line was measured, and the result described in Table 7.

TABLE 7

% Viability of HCEC as a function of *Sapindus mukorossi* extract concentration in shampoo (the shampoo's composition as described in table 1, except the % *Sapindus mukorossi* extract)

| Shampoo No. | *Sapindus mukorossi* extract (wt %) | Viability of HCEC (%) (±10%) |
|---|---|---|
| 2 | 1.5 | 100% |
| 1 | 2.25 | 50% |
| 3 | 3 | 22% |

As one can see, the highest viability was obtained when *Sapindus Mukorossi* extract concentration was the lowest and it may thus be determined that *Sapindus Mukorossi* extract is an irritant agent Example 2

Chamomile Extract

Chamomile extract is known for treating inflammation associated with hemorrhoids when applied topically. According to the prior art, chemical components of chamomile extract demonstrated anti-inflammatory, anti-hyperglycemic, anti-genotoxic, and anti-cancer properties. Hence we studied its ability to reduce eye irritation. However, the addition of chamomile extract (1 wt %) to Shampoo No. 3 under the same exposure conditions to Shampoo Nos. 1 to 3, did not change the viability percentage of HCEC, which remained about 22%.

Example 3

Film Creation on Top of the Eye
Lecithins Composition and Content

The viability percentage of HCEC as a function of lecithin type (egg or soy-bean) and their concentration in the shampoo were studied. The result described in Table 8.

The lecithins listed in Table 8, were added to the shampoo described in Table 6 (i.e., 0.8% soy-bean lecithin+0.5 egg yolk or 1% egg yolk+0.3% soy-bean lecithin).

TABLE 8

% Viability of HCEC as a function lecithins type in the shampoo (the shampoo's composition as described in Table 6, 3 wt % Sapindus extract)

| Lecithin type and percentage | Viability of HCEC (%) (±10%) |
|---|---|
| 0.5 wt % soy-bean lecithin (addition) | 20% |
| 0.5 wt % egg yolk (addition) | 60% |
| No addition | 22% |

As the results indicate, the addition of 0.5% of soy-ban lecithin did not change the viability percentage of HCEC. However, the addition of 0.5% of egg yolk improved the viability percentage significantly.

Example 4: Comparative Example

Shampoo Formulations Including

TABLE 9

Shampoo formulations

| Ingredient | Chemical Family |
|---|---|
| *Sapindus Mukorossi* extract | Saponins |
| *Camellia oleifera* extract | Saponins |
| *Quillaja* extract | Saponins |
| Aspen bark (*Populus tremuloides*) extract | Salicaceae |
| Soy-bean Lecithin | Phospholipids |
| Jojoba oil | Emollient |
| Squalene oil | Emollient |
| Egg Yolk | Phospholipids + cholesterol + Emollient |
| Sodium Hyaluronate | Poly saccharides |
| Xanthan gum | Poly saccharides |
| Carrageenan | Poly saccharides |
| Mannitol | Poly-ol |
| Glycerol | Poly-ol |
| Zemea | Poly-ol |
| Trehalose | Poly-ol |
| Perfume | |

Example 5

Reduction of Oils and Lecithins

The effect of oils and lecithin on the viability percentage of HCEC was tested in the shampoo described in Table 6, but in each test, one of the following ingredients was missed out (replaced by water).

TABLE 10

% Viability of HCEC as function of oil and lecithin absence in the shampoo (the shampoo composition as described in Table 6, except 2.25% Sapindus extract)

| missed out component | Viability of HCEC (%) (±10%) |
|---|---|
| oil | 20% |
| soya lecithin | 40% |
| Whole shampoo | 50% |

The results presented in Table 10 demonstrate that when oil or soy-bean lecithin was absent, the viability was reduced. The higher reduction obtained while the oil was absent.

Example 6

Hydrogel Creation

Hydrogels of sodium hyaluronate have been used for many years in ophthalmic surgery in Europe and in the U.S. to maintain the shape of the eye, to cover surgical instruments and to protect the corneal endothelium from damage, thus we test its influence.

Reduction of Sodium Hyaluronate

The effect of sodium hyaluronate absence on the viability percentage of HCEC was tested on the shampoo described in Table 6, but the sodium hyaluronate replaced by water.

TABLE 11

% Viability of HCEC as function of sodium hyaluronate absence in the shampoo (the shampoo composition as described in Table 7, except 2.25% Sapindus extract)

| missed out component | Viability of HCEC (%) (±10%) |
|---|---|
| Without sodium hyaluronate | 35% |
| Whole shampoo | 50% |

The results presented in Table 11 demonstrate that when sodium hyaluronate was absent, the viability was reduced.

Example 7

The Influence of Saponin Type
*Camellia oleifera* Seed Extract (Tea)
*Quillaja Saponaria* Extract
*Saponaria officinalis* Extract In order to compare the effect of the saponin extracts from different plants, the *Quillaja* extract (Table 6) was replaced once with *Camellia* extract, and seconds with *Saponaria* extract (All shampoos contained 2.25 wt % *Sapindus* extract).

TABLE 12

% Viability of HCEC as a function of saponins type in the shampoo (the shampoo composition as described in Table 6, except 2.25% Sapindus extract)

| Saponin type | Viability of HCEC (%) (±10%) |
|---|---|
| *Quillaja* extract | 50% |
| *Camellia* extract | 100% |
| *Saponaria* extract | 100% |

As the results indicate, the viability percentage increased significantly when *Quillaja* replaced by *Camellia* or *Saponaria* extracts.

In Vivo Methods

One drop of diluted shampoo; 6 wt. % by saline, was instilled into one volunteers' eye, and one drop of saline his other eye. Each shampoo's composition was examined on 10 volunteers. The evaluations of the eye irritation criteria were as follows:

The intensity of eye irritation: burning, stinging and/or itching according to the following scale:
None
Slight prickling, tingling and/or slight burning and/or stinging and/or slight itching
Moderate burning and/or stinging and/or moderate itching
Severe burning and/or stinging and/or strong itching The evaluations of the eye irritation were done immediately after the after 8-10 min, 15 min, and 1 hour. The scores were collected, and average of the scores is appearing in the following tables.

The study was accompanied by an ophthalmologist.

Egg Yolk Concentration

The eye irritation of shampoos containing different egg yolk concentration was studied, and the result described in Table 13.

TABLE 13 irritation average score as a function of egg yolk concentration (shampoo composition as described in Table 6)

| Egg yolk concentration (wt %) | Average Score |
|---|---|
| 0 | $2.5_{(\pm 0.4)}$ |
| 0.5 | $1.1_{(\pm 0.3)}$ |
| 1.5 | $0.2_{(\pm 0.3)}$ |

As one can see in Table 13, significant reduction in eye irritation was obtained while increasing the egg yolk concentration.

Chamomile Extract

The effect of chamomile extract (1 wt % addition) on eye irritation was tested in the shampoo described in Table 6.

TABLE 14 irritation average score as a function of chamomile addition (shampoo composition as described in Table 6)

| Chamomile addition | Average Score |
|---|---|
| No addition | $1.1_{(\pm 0.3)}$ |
| 1 wt % chamomile addition | $1.3_{(\pm 0.3)}$ |

The addition of chamomile extract to shampoo didn't improve the eye irritation as was demonstrated also at the in-vitro test.

Sodium Hyaluronate

The effect of sodium hylorunate on eye irritation was tested in the shampoo described in Table 6, with or without sodium hylorunate.

TABLE 15 irritation average score with or without sodium hylorunate (shampoo composition as described in Table 7, 5 wt % egg yolk)

| Sodium hyaluronate addition | Average Score |
|---|---|
| With 0.05 wt % sodium hylorunate | $0.2_{(\pm 0.3)}$ |
| Without sodium hylorunate | $1_{(\pm 0.3)}$ |

The eye irritation was decreased significantly when the shampoo content 0.05 wt % of sodium hylorunate.

Example 8: Haemolysis Test

Haemolysis test (which serves as a model for eye irritation) is conducted in order to determine the safety of the products of the invention in comparison to the commercial surfactant SLES (sodium lauryl ether sulfate).

Preparation of the erythrocyte suspension: erythrocytes of sheep blood is separated by centrifugation at 1250 g, for 15 minutes at room temperature, wash three times with phosphate-buffered saline solution (PBS, pH 7.4), and centrifuge twice under the same condition. The blood volume is completed with PBS. This suspension is maintained at 4 degrees centigrade for up to three days.

The assay procedure: 20 μL of each sample are diluted up to ml of the suspension, and are incubated with for 30 minutes in ice. The incubation is terminated by a rapid, high-speed (1800 g) centrifugation for 30 minutes. The extent of haemolysis is determined in spectrophotometrically at 540 nm against a blank (PBS). The extent of haemolysis, expressed as a percentage, is calculated as the absorbance of an erythrocyte suspension incubated with each product, relative to that of a completely haemolysed control (100 percent, at distilled water) at 540 nm. The Hm50 (50 percent haemolysis) is determined from concentration-response curves.

| Hm50 |
|---|

The invention claimed is:
1. A method for reducing, diminishing or ameliorating irritation to an eye region or to a skin region surrounding the eye, the method comprising topically administering to the eye region or to the skin region surrounding the eye a formulation selected from the group consisting of:
- (i) soy-bean lecithin, jojoba oil, squalene oil, egg yolk and sodium hyaluronate;
- (ii) soy-bean lecithin, jojoba oil, squalene oil, egg yolk and at least one polysaccharide selected from sodium hyaluronate, xanthan gum and carrageenan;
- (iii) soy-bean lecithin, jojoba oil, squalene oil, egg yolk and at least one polyol selected from mannitol, glycerol, zemea and trehalose; and
- (iv) soy-bean lecithin, jojoba oil, squalene oil, egg yolk, at least one polysaccharide selected from sodium hyaluronate, xanthan gum and carrageenan, and at least one polyol selected from mannitol, glycerol, zemea and trehalose.

2. The method according to claim 1, wherein the formulation is selected from the group consisting of (A) a baby shampoo, baby bath, mild skin cleanser, facial skin cleanser, sensitive skin cleanser and cleansing formulations suitable for use on human infant skin; or from the group consisting of (B) adult shampoo, adult bath, mild skin cleanser, facial skin cleanser, sensitive skin cleanser and cleansing formulations suitable for use on human adult skin.

3. The method according to claim 1, wherein the formulation further comprising at least one additional additive selected from the group consisting of phospholipids, polysaccharides, polyols, saponins, salicilates, preservatives, perfumes, natural coloring agents, emollients, non-aqueous or aqueous solvents or mixtures, and other active or non-active components.

4. The method according to claim 1, wherein the formulation further comprising at least one preservative.

5. The method according to claim 1, wherein the formulation further comprising at least one saponin.

6. A method of reducing, diminishing or ameliorating irritation to an eye region or to a skin region surrounding the eye, said irritation being associated with at least one skin care formulation, the method comprising adding on to said skin care formulation a formulation according to claim 1 to obtain an add on formulation, wherein said skin care formulation is selected from the group consisting of (A) a baby shampoo, baby bath, mild skin cleanser, facial skin cleanser, sensitive skin cleanser and cleansing formulations suitable for use on human infant skin; or from the group consisting of (B) adult shampoo, adult bath, mild skin cleanser, facial skin cleanser, sensitive skin cleanser and cleansing formulations suitable for use on human adult skin.

7. The method according to claim 6, wherein the add on formulation comprises at least one saponin selected from the group consisting of *Sapindus mukorossi* extract, *Camellia oleifera* extract and *Quillaja* extract; Aspen bark extract; soy-bean lecithin; Jojoba oil; Squalene oil; Egg yolk; at least one polysaccharide selected from sodium hyaluronate, xanthan gum and carrageenan; and at least one polyol selected from mannitol, glycerol, zemea and trehalose.

8. A method for suppressing or reducing ocular irritancy of a pre-made cosmetic or therapeutic formulation or an ophthalmic formulation suitable for application to an eye of a subject or to a skin region surrounding an eye of a subject, the cosmetic or therapeutic formulation being capable of causing irritation to an ocular membrane or to the eye's cornea, the method comprising adding on to said pre-made cosmetic or therapeutic formulation or an ophthalmic formulation a formulation according to claim 1.

9. The method of claim 6, wherein the add on formulation comprises *Sapindus mukorossi* extract, *Camellia oleifera* extract, *Quillaja* extract, Aspen bark extract, soy-bean lecithin, jojoba oil, squalene oil, egg yolk, at least one polysaccharide selected from sodium hyaluronate, xanthan gum and carrageenan; and at least one polyol selected from mannitol, glycerol, zemea and trehalose.

10. The method of claim 6, wherein the add on formulation comprises 0.5-6 wt % of *Sapindus mukorossi* extract; 0.1-6 wt % of *Camellia oleifera* extract; 0.1-6 wt % of *Quillaja* extract; 0.1-0.8 wt % of Aspen bark extract; 0.1-5 wt % of soy-bean lecithin; 0.2-4 wt % of jojoba oil; 0.2-4 wt % of squalene oil; 0.2-5 wt % of egg yolk; at least one polysaccharide selected from sodium hyaluronate up to 0.8 wt %, xanthan gum up to 2.5 wt % and carrageenan up to 2.5 wt %; at least one polyol selected from mannitol up to 2.5 wt % and glycerol up to 2.5 wt %, and optionally zemea up to 15 wt % and/or trehalose up to 2.5 wt %; and optionally perfume up to 1.5 wt %.

\* \* \* \* \*